(12) United States Patent
Gerber et al.

(10) Patent No.: US 8,478,411 B2
(45) Date of Patent: *Jul. 2, 2013

(54) FLEXIBLE TUBE SENSOR FOR SENSING URINARY SPHINCTER PRESSURE

(75) Inventors: Martin T. Gerber, Maple Grove, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/279,826

(22) Filed: Oct. 24, 2011

(65) Prior Publication Data

US 2012/0041510 A1 Feb. 16, 2012

Related U.S. Application Data

(62) Division of application No. 11/116,952, filed on Apr. 28, 2005, now Pat. No. 8,068,910.

(51) Int. Cl.
*A61N 1/00* (2006.01)

(52) U.S. Cl.
USPC ............................ 607/41; 607/62; 600/587

(58) Field of Classification Search
None
See application file for complete search history.

(56) References Cited

U.S. PATENT DOCUMENTS

| | | | |
|---|---|---|---|
| 3,789,667 A | 2/1974 | Porter et al. | |
| 4,146,029 A | 3/1979 | Ellinwood, Jr. | |
| 4,519,401 A | 5/1985 | Ko et al. | |
| 4,846,191 A | 7/1989 | Brockway et al. | |
| 4,934,996 A | 6/1990 | Mohl et al. | |
| RE33,360 E | 10/1990 | Reynolds et al. | |
| 5,018,529 A | 5/1991 | Tenerz et al. | |
| 5,103,835 A | 4/1992 | Yamada et al. | |
| 5,109,870 A | 5/1992 | Silny et al. | |
| 5,134,281 A | 7/1992 | Bryenton et al. | |
| 5,207,648 A | 5/1993 | Gross | |
| 5,297,437 A | 3/1994 | Schneider | |
| 5,396,897 A | 3/1995 | Jain et al. | |
| 5,554,139 A | 9/1996 | Okajima | |
| 5,573,007 A | 11/1996 | Bobo, Sr. | |
| 6,015,393 A | 1/2000 | Hovland et al. | |

(Continued)

FOREIGN PATENT DOCUMENTS

EP 0 694 284 A1 1/1996

OTHER PUBLICATIONS

Coosemans et al., "Datalogger for Bladder Pressure Monitoring with Wireless Power and Data Transmission," Katholieke Universiteit Leuven, Department ESAT-MICAS, Belgium, 1 pg. (Oct. 17, 2003).

(Continued)

*Primary Examiner* — Mark W Bockelman

(57) ABSTRACT

The disclosure describes a therapeutic sphincter control system with a fluid tube pressure sensor. The system senses sphincter pressure and sends the information to a stimulator that is capable of stimulation therapy to control sphincter contractility, thus reducing unwanted urinary incontinence. Measuring sphincter pressure is accomplished through the use of a fluid-filled tube placed through the sphincter and attached to a module implanted within the bladder. Pressure within the tube is transduced to generate an electrical signal that is sent wirelessly to an implanted stimulator connected to a lead positioned near pelvic floor nerves. An external device may be used to wirelessly send information to the implanted stimulator and inhibit stimulation in order for the patient to empty the bladder. Pressure information and stimulation information may be recorded and reviewed for continued patient monitoring. In addition, the system may only include the pressure sensor to monitor patient pressure information.

21 Claims, 10 Drawing Sheets

U.S. PATENT DOCUMENTS

| | | | |
|---|---|---|---|
| 6,162,188 | A | 12/2000 | Barnea |
| 6,354,991 | B1 | 3/2002 | Gross et al. |
| 6,360,123 | B1 | 3/2002 | Kimchi et al. |
| 6,393,323 | B1 | 5/2002 | Sawan et al. |
| 6,473,651 | B1 | 10/2002 | Kuzma et al. |
| 6,650,943 | B1 | 11/2003 | Whitehurst et al. |
| 6,652,449 | B1 | 11/2003 | Gross et al. |
| 6,689,056 | B1 | 2/2004 | Kilcoyne et al. |
| 7,328,070 | B2 | 2/2008 | Gerber et al. |
| 7,610,093 | B2 | 10/2009 | Gerber et al. |
| 7,613,516 | B2 | 11/2009 | Cohen et al. |
| 7,623,923 | B2 | 11/2009 | Gerber et al. |
| 8,068,910 | B2 | 11/2011 | Gerber et al. |
| 2002/0055761 | A1 | 5/2002 | Mann et al. |
| 2002/0062060 | A1 | 5/2002 | Gross et al. |
| 2002/0103424 | A1 | 8/2002 | Swoyer et al. |
| 2002/0111586 | A1 | 8/2002 | Mosel et al. |
| 2003/0100929 | A1 | 5/2003 | Forsell |
| 2003/0100930 | A1 | 5/2003 | Cohen et al. |
| 2003/0220292 | A1 | 11/2003 | Okada et al. |
| 2003/0236557 | A1 | 12/2003 | Whitehurst et al. |
| 2003/0236558 | A1 | 12/2003 | Whitehurst et al. |
| 2004/0015204 | A1 | 1/2004 | Whitehurst et al. |
| 2004/0015205 | A1 | 1/2004 | Whitehurst et al. |
| 2004/0147871 | A1 | 7/2004 | Burnett |
| 2004/0152999 | A1 | 8/2004 | Cohen et al. |
| 2005/0065408 | A1 | 3/2005 | Benderev |
| 2005/0177067 | A1 | 8/2005 | Tracey et al. |
| 2005/0245840 | A1 | 11/2005 | Christopherson et al. |
| 2005/0288603 | A1 | 12/2005 | Goping |

OTHER PUBLICATIONS

Siwapornsathain et al., "A Telemetry and Sensor Platform for Ambulatory Urodynamics," Department of Electrical and Computer Engineering, University of Wisconsin, Madison, WI, 5 pgs. (2002).

Van Waalwijk van Doorn, "Standardisation of Ambulaatory Urodynamic Monitoring," Report of the Standarisation Sub-committee of the ICS ambulatory urodynamic studies, 21 pgs. (2000).

"Wireless Physiological Pressure Transducer," MEMSCAP Sensor Solutions, 2 pgs. (May 2003).

Restriction Requirement from U.S. Appl. No. 11/116,952, dated Mar. 24, 2008, 7 pp.

Response to Restriction Requirement dated Mar. 24, 2008, from U.S. Appl. No. 11/116,952, filed Apr. 16, 2008, 1 p.

Office Action from U.S. Appl. No. 11/116,952, dated Jul. 14, 2008, 7 pp.

Response to Office Action dated Jul. 14, 2008, from U.S. Appl. No. 11/116,952, filed Oct. 14, 2008, 10 pp.

Office Action from U.S. Appl. No. 11/116,952, dated Jan. 27, 2009, 7 pp.

Response to Office Action dated Jan. 27, 2009, from U.S. Appl. No. 11/116,952, filed Apr. 27, 2009, 5 pp.

Office Action from U.S. Appl. No. 11/116,952, dated Aug. 6, 2009, 8 pp.

Response to Office Action dated Aug. 6, 2009, from U.S. Appl. No. 11/116,952, filed Nov. 2, 2009, 7 pp.

Office Action from U.S. Appl. No. 11/116,952, dated Mar. 11, 2010, 7 pp.

Response to Office Action dated Mar. 11, 2010, from U.S. Appl. No. 11/116,952, filed Jul. 7, 2010, 10 pp.

Office Action from U.S. Appl. No. 11/116,952, dated Mar. 31, 2011, 10 pp.

Notice of Allowance from U.S. Appl. No. 11/116,952, dated Jun. 30, 2011, 8 pp.

Supplemental Notice of Allowability from U.S. Appl. No. 11/116,952, dated Sep. 22, 2011, 2 pp.

Response after Notice of Allowance from U.S. Appl. No. 11/116,952, filed Sep. 29, 2011, 4 pp.

Examiner's Response to Rule 312 Communication, dated Oct. 13, 2011, 2 pp.

Restriction Requirement from U.S. Appl. No. 11/117,064, dated Mar. 25, 2008, 6 pp.

Response to Restriction Requirement dated Mar. 25, 2008, from U.S. Appl. No. 11/117,064, filed Apr. 24, 2008, 1 p.

Office Action from U.S. Appl. No. 11/117,064, dated Jul. 15, 2008, 8 pp.

Response to Office Action dated Jul. 15, 2008, from U.S. Appl. No. 11/117,064, filed Oct. 15, 2008, 5 p.

Office Action from U.S. Appl. No. 11/117,064, dated Dec. 31, 2008, 4 pp.

Response to Office Action dated Dec. 31, 2008, from U.S. Appl. No. 11/117,064, filed Mar. 31, 2009, 5 pp.

Notice of Allowance from U.S. Appl. No. 11/117,064, dated Jun. 18, 2009, 4 pp.

Office Action from U.S. Appl. No. 11/117,079, dated Jul. 3, 2006, 11 pp.

Response to Office Action dated Jul. 3, 2006, from U.S. Appl. No. 11/117,079, filed Oct. 2, 2006, 15 pp.

Office Action from U.S. Appl. No. 11/117,079, dated Dec. 8, 2006, 12 pp.

Response to Office Action dated Dec. 8, 2006, from U.S. Appl. No. 11/117,079, filed Mar. 8, 2007, 22 pp.

Advisory Action from U.S. Appl. No. 11/117,079, dated Apr. 3, 2007, 3 pp.

Response to Advisory Action dated Apr. 3, 2007, from U.S. Appl. No. 11/117,079, filed Jun. 7, 2007, 14 pp.

Notice of Allowance for U.S. Appl. No. 11/117,079, dated Aug. 17, 2007, 7 pp.

Restriction Requirement from U.S. Appl. No. 11/117,054, dated Mar. 6, 2007, 6 pp.

Response to Restriction Requirement dated Mar. 6, 2007, from U.S. Appl. No. 11/117,054, filed Apr. 6, 2007, 2 pp.

Office Action from U.S. Appl. No. 11/117,054, dated Apr. 19, 2007, 8 pp.

Response to Office Action dated Apr. 19, 2007, from U.S. Appl. No. 11/117,054, filed Jul. 19, 2007, 14 pp.

Office Action from U.S. Appl. No. 11/117,054, dated Oct. 2, 2007, 9 pp.

Response to Office Action dated Oct. 2, 2007, from U.S. Appl. No. 11/117,054, filed Dec. 7, 2007, 13 pp.

Advisory Action from U.S. Appl. No. 11/117,054, dated Dec. 31, 2007, 3 pp.

Office Action from U.S. Appl. No. 11/117,054, dated Mar. 19, 2008, 7 pp.

Response to Office Action dated Mar. 19, 2008, from U.S. Appl. No. 11/117,054, filed Jun. 19, 2008, 17 pp.

Office Action from U.S. Appl. No. 11/117,054, dated Sep. 25, 2008, 9 pp.

Response to Office Action dated Sep. 25, 2008 from U.S. Appl. No. 11/117,054, filed Nov. 25, 2008, 8 pp.

Notice of Allowance from U.S. Appl. No. 11/117,054, dated Dec. 18, 2008, 4 pp.

Office Action from U.S. Appl. No. 11/117,054, Jan. 21, 2009, 7 pp.

Response to Office Action dated Jan. 21, 2009, from U.S. Appl. No. 11/117,054, filed Apr. 21, 2009, 3 pp.

Notice of Allowance from U.S. Appl. No. 11/117,054, dated Jul. 14, 2009, 4 pp.

FLEXIBLE TUBE SENSOR FOR SENSING URINARY SPHINCTER PRESSURE

RELATED APPLICATION

This application is a divisional of U.S. Pat. No. 8,068,910, issued Nov. 29, 2011 and entitled "FLEXIBLE TUBE SENSOR FOR SENSING URINARY SPHINCTER PRESSURE," the entire content of which is incorporated herein by reference.

TECHNICAL FIELD

The invention relates to implantable medical devices and, more particularly, implantable sensors.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Electrical stimulation of nerves in the pelvic floor may provide an effective therapy for a variety of disorders, including urinary incontinence. For example, an implantable neurostimulator may be provided to deliver electrical stimulation to the sacral nerve to induce sphincter constriction and thereby close or maintain closure of the urethra at the bladder neck. An appropriate course of neurostimulation therapy may be aided by a sensor that monitors physiological conditions with the urinary tract. In some cases, an implantable stimulation device may deliver stimulation therapy based on the level or state of a sensed physiological condition.

SUMMARY

The invention is directed to a flexible tube sensor that is implantable to sense urinary sphincter pressure, as well as a neurostimulation system and method that make use of such a sensor for alleviation of urinary incontinence. The sensor includes a thin, flexible tube containing a volume of fluid and a sensing element to detect pressure levels within the tube. The flexible tube is deployed within the bladder neck to transduce pressure exerted by the urinary sphincter as a function of the pressure within the fluid tube.

Inadequate sphincter pressure may result in involuntary bladder voiding, i.e., incontinence. The flexible tube sensor may provide short- or long-term monitoring of urinary sphincter pressure, e.g., for analysis by a clinician. Alternatively, a flexible tube sensor may form part of a closed-loop neurostimulation system. For example, neurostimulation therapy can be applied to increase sphincter pressure, and thereby prevent involuntary urine leakage. In particular, an implantable neurostimulator may be responsive to urinary sphincter pressure signals generated by a flexible tube sensor, as described herein, to provide closed loop neurostimulation therapy to alleviate incontinence.

In one embodiment, the invention provides an implantable electrical stimulation system comprising an implantable pressure sensor including a flexible tube containing fluid and a sensing element that senses a pressure level exerted by a sphincter within a patient based on a pressure level of the fluid when the tube is placed proximate to the sphincter, and an implantable stimulator that delivers electrical stimulation to the patient based on the sensed pressure level.

In another embodiment, the invention provides a method comprising sensing a pressure level exerted by a sphincter within a patient based on a pressure of fluid within a flexible tube placed proximate to the sphincter, and delivering electrical stimulation to the patient based on the sensed pressure level.

In an additional embodiment, the invention provides an implantable pressure sensor comprising a flexible tube containing fluid, a pressure sensing element that senses a pressure level of the fluid within the flexible tube, a fixation mechanism to position the flexible tube proximate a sphincter within a patient, and a circuit that determines a pressure level of the sphincter based on the sensed pressure level.

Although the invention may be especially applicable to sensing urinary sphincter pressure, the invention alternatively may be applied more generally to other sphincters within the patient, such as the lower esophageal sphincter (LES) or pyloric sphincter. In addition, in those instances, the invention may be adapted to support electrical stimulation of other body organs, such as the stomach or intestines, e.g., for treatment of obesity or gastric motility disorders.

In various embodiments, the invention may provide one or more advantages. For example, the use of a thin, flexible tube sensor permits pressure to be sensed within the narrow, constricted passage proximate the urinary sphincter. In this manner, pressure can be sensed without significantly obstructing or altering the physiological function or the urinary sphincter.

The flexible tube sensor may be coupled to a larger sensor housing that resides within the bladder and houses sensor electronics for transducing a pressure level of the fluid in the tube, as well as telemetry electronics. The flexible tube sensor permits pressure information to be obtained on a continuous or periodic basis as the patient goes about a daily routine. In addition, the flexible nature of the tube permits the sensor to be implanted in a variety of locations, and to be constructed in a variety of shapes and sizes.

The flexible tube sensor may transmit sensed pressure information to an implantable stimulator to permit dynamic control of the therapy delivered by the stimulator on a closed-loop basis. For example, the stimulator may adjust stimulation parameters, such as amplitude, pulse width or pulse rate, in response to the sensed pressure. In this manner, the stimulator can provide enhanced efficacy and prevent involuntary leakage. In addition, or alternatively, adjustment may involve on and off cycling of the stimulation in response to pressure levels indicative of a particular bladder fill stage. For example, stimulation may be turned off until the pressure level exceeds a threshold indicative of a particular fill stage of the bladder.

Also, with closed-loop stimulation, the stimulator may generate stimulation parameter adjustments that more effectively target the function of the urinary sphincter muscle, thereby enhancing stimulation efficacy. In some patients, more effective stimulation via the sacral nerve may actually serve to strengthen the sphincter muscle, restoring proper operation.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
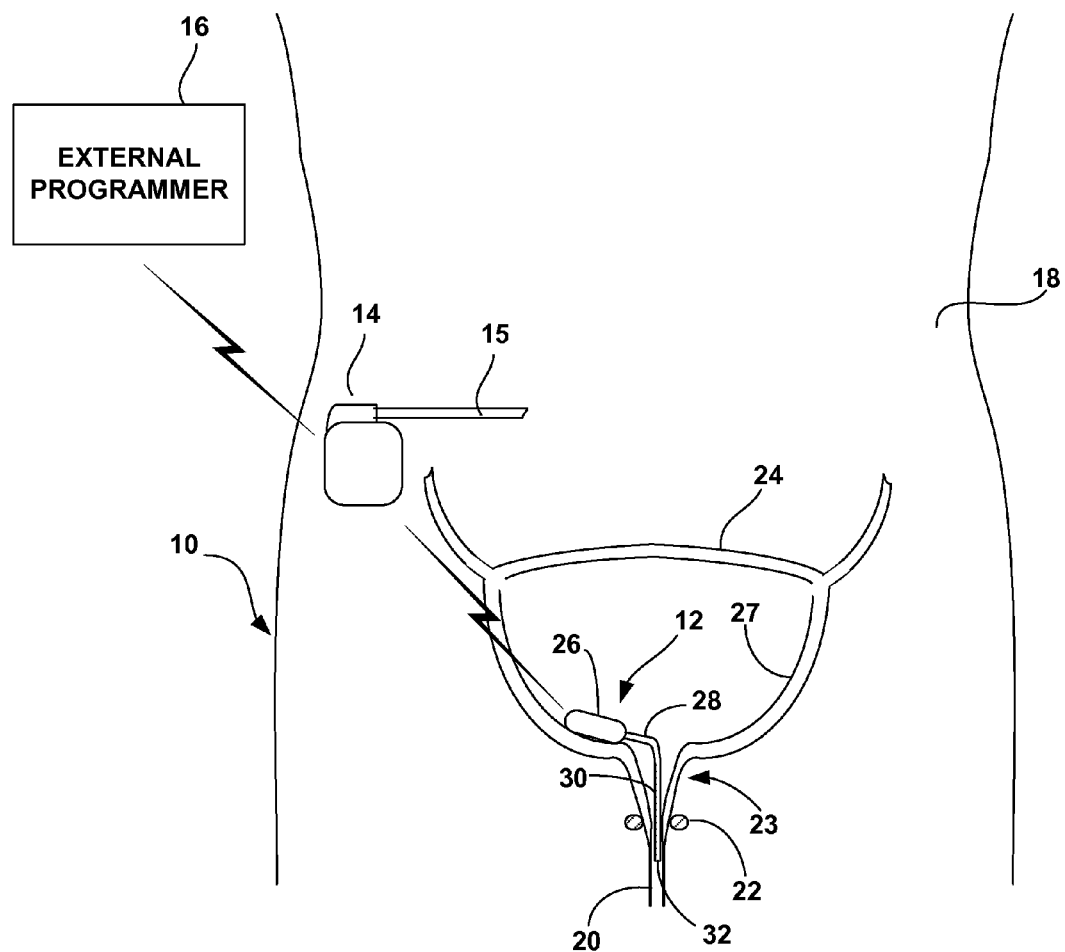
FIG. 1 is a schematic diagram illustrating an implantable stimulation system, incorporating a urinary sphincter pressure sensor, for alleviation of urinary incontinence.

FIG. 1 is a schematic diagram illustrating an implantable stimulation system 10 for alleviation of urinary incontinence. As shown in FIG. 1, system 10 may include an implantable pressure sensor 12, implantable stimulator 14 and external programmer 16 shown in conjunction with a patient 18. Pressure sensor 12 senses a pressure level exerted by urinary sphincter 22 on urethra 20 proximate the neck 23 of bladder 24, and transmits pressure information based on the sensed pressure level to at least one of stimulator 14 and programmer 16 by wireless telemetry. Stimulator 14 or programmer 16 may record the information, generate adjustments to electrical stimulation parameters applied by the stimulator, or both. In some embodiments, pressure sensor 12 may support purely diagnostic purposes, such as urodynamic study, e.g., by transmission of information to external programmer 16. In other embodiments, pressure sensors 12 may form part of a closed loop feedback system for stimulator 14.

Figure 2:
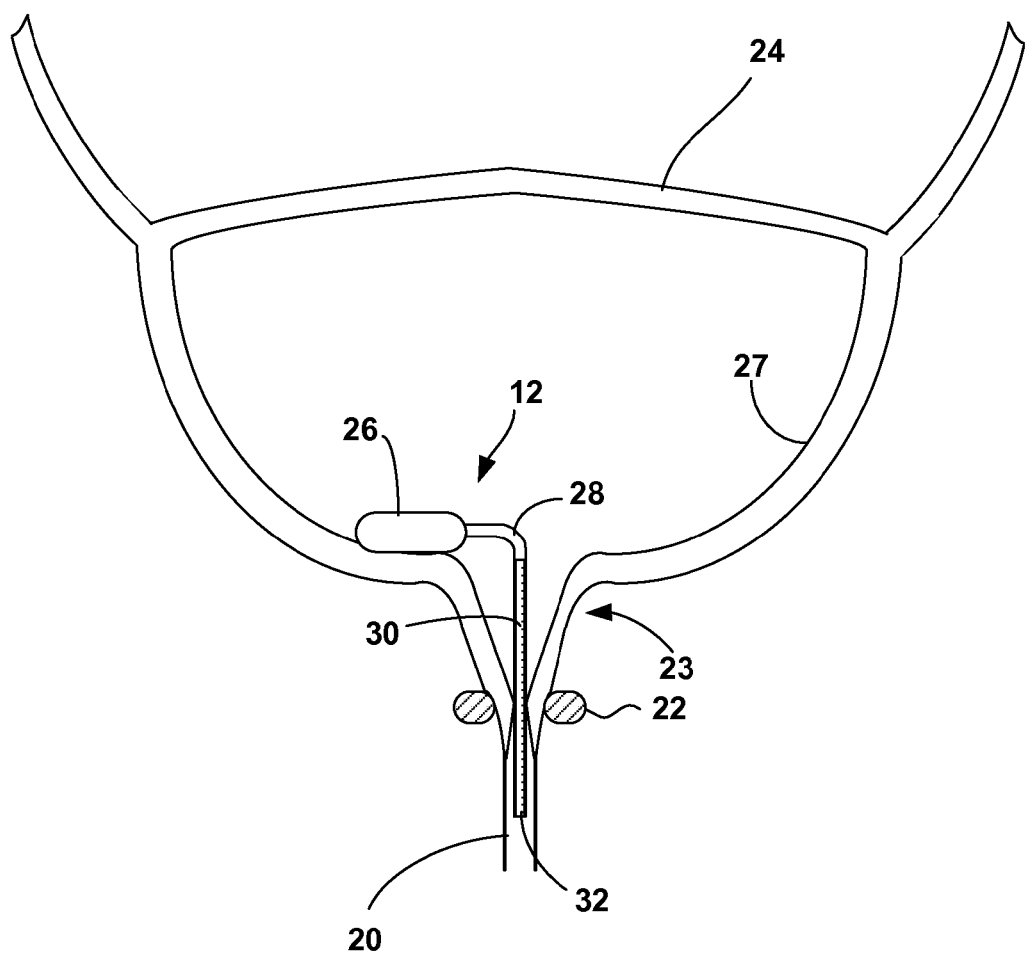
FIG. 2 is an enlarged schematic diagram illustrating an implantable pressure sensor with a flexible tube extending through the urinary sphincter of a patient.

FIG. 2 is an enlarged schematic diagram illustrating implantable pressure sensor 12 As shown in FIGS. 1 and 2, pressure sensor 12 includes a sensor housing 26 and a flexible tube 28 that extends from the housing. Flexible tube 28 contains a volume of fluid 30, and includes a closed end 32 and an open end (not shown in FIG. 1). Sensor housing 26 contains a sensing element (not shown in FIG. 1) adjacent the open end of flexible tube 28. The sensing element senses pressure level within flexible tube 28. Sensor housing 26 further contains electronics to generate pressure information, and telemetry circuitry for transmission of the information.

As further shown in FIGS. 1 and 2, sensor housing 26 may reside within bladder 24. Sensor housing 26 may be temporarily or permanently attached to an inner wall 27 of bladder 24, such as the mucosal lining, as will be described. Alternatively, housing 26 may be implanted sub-mucosally. Flexible tube 28 extends away from sensor housing 26 and through an inner lumen defined by the bladder neck proximate urinary sphincter 22. In this manner, flexible tube 28 is positioned to directly sense the pressure level exerted by urinary sphincter 22. Yet, flexible tube 28 may be sufficiently thin to avoid significant obstruction of urethra 20 or disruption of the function of urinary sphincter.

As a further alternative, housing 26 may reside outside bladder 24, in which case flexible tubes 28, 29 may extend into bladder 24 and through urinary sphincter 22 through a hole formed in the bladder. In this case, housing 26 may be surgically or laparoscopically implanted within the abdomen. Tube 28 may be surgically or laparoscopically guided through a hole in the wall of bladder 24. A cystoscope may be used to grab tube 28 and pull it downward through urinary sphincter 22 and urethra 20. In some embodiments, housing 26 and its contents may be integrated with stimulator 14, in which case flexible tube 28 extends from the stimulator housing and into bladder 24, much like leads carrying stimulation or sense electrodes.

With further reference to FIG. 1, implantable stimulator 14 includes an electrical lead 15 (partially shown in FIG. 1) carrying one or more electrodes that are placed at a nerve site within the pelvic floor. For example, the electrodes may be positioned to stimulate the sacral nerve and thereby innervate urinary sphincter 22. In particular, electrical stimulation may be applied to cause urinary sphincter 22 to increase closing pressure to avoid involuntary leakage from bladder 24. Alternatively, if voluntary voiding is desired by patient 18, electrical stimulation can be suspended or reduced to reduce the closing pressure exerted by urinary sphincter 22 on urethra 20 at the bladder neck.

For spinal cord injury patients who cannot perceive a sensation of bladder fullness, sphincter pressure sensed by pressure sensor 12 may be transmitted to external programmer 16, with or without an accompanying stimulator 14, to advise the patient when urinary sphincter pressure is high, indicating bladder fullness. In this case, the advice may be in the form of a audible, visual or vibratory stimulus. In response to the advice, the spinal cord injury patient is able to catheterize the urethra 20 and bladder 24 to voluntarily relieve urine.

Implantable stimulator 14 delivers stimulation therapy to the sacral nerve in order to keep the sphincter 22 constricted and keep contents of bladder 24 from leaking out through urethra 20. At predetermined times, or at patient controlled instances, the external programmer 16 may program stimulator 14 to interrupt the stimulation to allow the sphincter to relax, thus permitting voiding of bladder 24. Upon completion of the voiding event, external programmer 16 may program stimulator 14 to resume stimulation therapy and thereby maintain closure of urinary sphincter 22.

In this manner, implantable stimulator 14 delivers stimulation therapy to the sacral nerve in order to keep the sphincter 22 constricted and keep contents of bladder 24 from leaking out through urethra 20. At predetermined times or at patient controlled instances, the external programmer 16 may program stimulator 14 to interrupt the stimulation to allow the sphincter to relax, thus permitting voiding of bladder 24. Upon completion of the voiding event, external programmer 16 may program stimulator 14 to resume stimulation therapy and thereby maintain closure of urinary sphincter 22.

In addition, adjustment of stimulation parameters may be responsive to pressure information transmitted by implantable pressure sensor 12. For example, external programmer 16 or implantable stimulator 14 may adjust stimulation parameters, such as amplitude, pulse width, and pulse rate, based on pressure information received from implantable sensor 12. In this manner, implantable stimulator 14 adjusts stimulation to either increase or reduce urinary sphincter pressure based on the actual pressure level exerted by urinary sphincter 22. Pressure sensor 12 may transmit pressure information periodically, e.g., every few seconds, minutes or hours. In some embodiments, pressure sensor 12 may transmit pressure information when there is an abrupt change in sphincter pressure, e.g., a pressure change that exceeds a predetermined threshold. In addition to parameter adjustments, or alternatively, adjustment may involve on and off cycling of the stimulation in response to pressure levels indicative of a particular bladder fill stage. For example, stimulation may be turned off until the pressure level exceeds a threshold indicative of a particular fill stage of the bladder, at which time stimulation is turned on. Then, stimulation parameters may be further adjusted as the sensed pressure level changes.

External programmer 16 may be a small, battery-powered, portable device that accompanies the patient 18 throughout a daily routine. Programmer 16 may have a simple user interface, such as a button or keypad, and a display or lights. Patient 18 may initiate a voiding event, i.e., a voluntary voiding of bladder 24, via the user interface. In some embodiments, the length of time for a voiding event may be determined by pressing and holding down a button for the duration of a voiding event, pressing a button a first time to initiate voiding and a second time when voiding is complete, or by a predetermined length of time permitted by programmer 16 or implantable stimulator 14. In each case, programmer 16 causes implantable stimulator 14 to temporarily terminate stimulation so that voluntary voiding is possible.

In some embodiments, stimulator 14 may immediately recommence stimulation upon completion of a voiding event, and thereafter adjust stimulation parameters based on pressure information generated by implantable sensor 12. Alternatively, stimulator 14 may terminate stimulation upon initiation of a voiding event, and recommence stimulation only after implantable pressure sensor 12 measures a decrease of pressure in the urethra 20 that corresponds to bladder 24 being empty. As a further alternative, following completion of the voiding event, stimulator 14 may wait to recommence stimulation until pressure sensor 12 detects generation of an inadequate pressure level by urinary sphincter 22, which could result in involuntary leakage. In this case, stimulator 14 recommences stimulation to enhance urinary sphincter pressure.

Implantable stimulator 14 may be constructed with a biocompatible housing, such as titanium or stainless steel, or a polymeric material such as silicone or polyurethane, and surgically implanted at a site in patient 18 near the pelvis. The implantation site may be a subcutaneous location in the side of the lower abdomen or the side of the lower back. One or more electrical stimulation leads 15 are connected to implantable stimulator 14 and surgically or percutaneously tunneled to place one or more electrodes carried by a distal end of the lead at a desired nerve site, such as a sacral nerve site within the sacrum.

In the example of FIGS. 1 and 2, sensor housing 26 of implantable pressure sensor 12 is attached to the inner wall 27 of bladder 24 near bladder neck 23. However, the attachment site for sensor housing 26 could be anywhere with access to urinary sphincter 22. With a relatively long flexible tube 28, for example, sensor housing 26 could be positioned at a greater distance from bladder neck 23. Also, in some embodiments, sensor housing 26 could be attached within urethra 20, e.g., downstream from urinary sphincter 22, although attachment of the sensor housing within bladder 24 may be desirable to avoid possible obstruction of the urethra.

Figure 3:
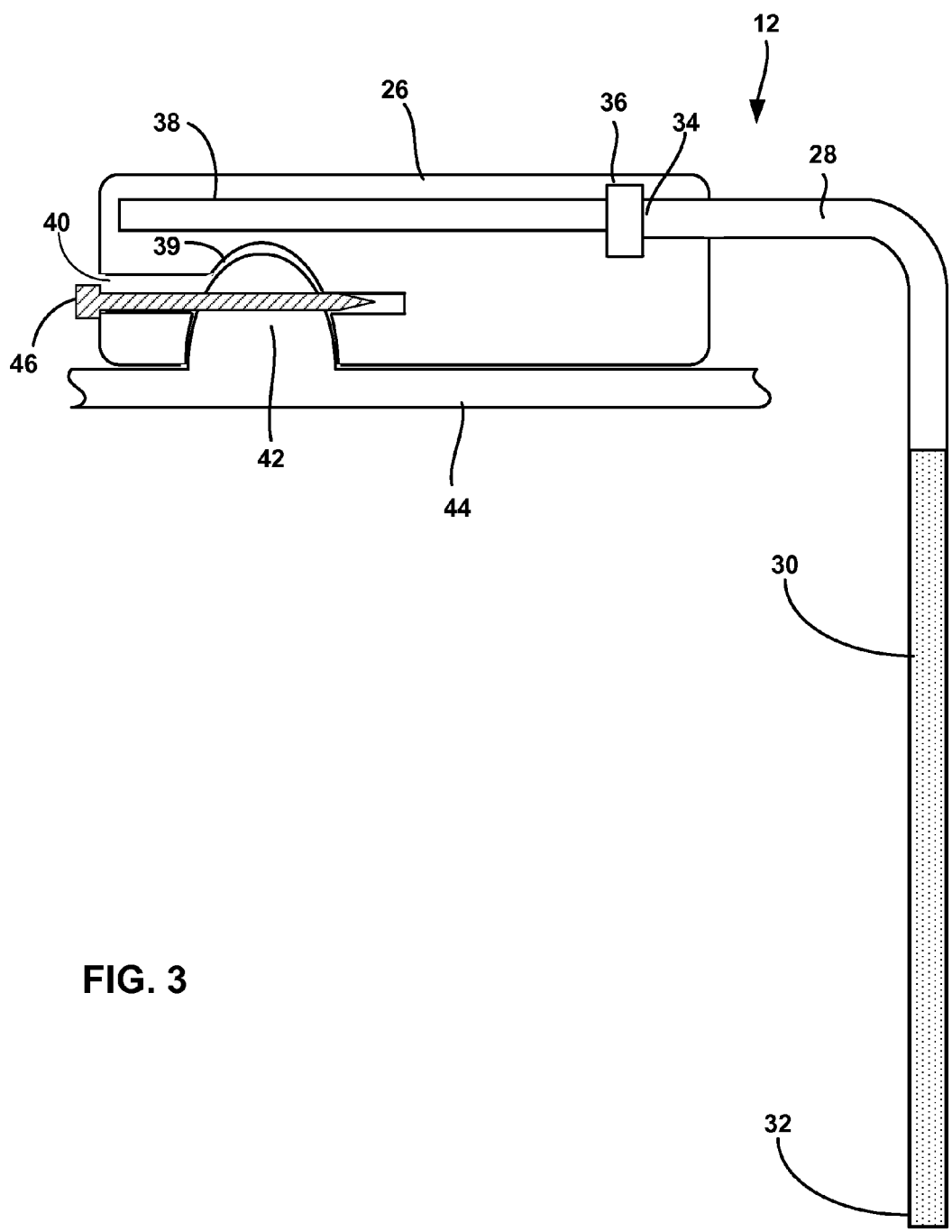
FIG. 3 is an enlarged, cross-sectional side view of the implantable pressure sensor of FIGS. 1 and 2.

FIG. 3 is an enlarged, cross-sectional side view of the implantable pressure sensor 12 of FIGS. 1 and 2. FIG. 3 is a conceptual illustration. As shown in FIG. 3, sensor housing 26 receives an open end 34 of flexible tube 28. A sensing element 36 is mounted within sensor housing 26, at open end 34, to sense a pressure level within fluid tube 28. Sensing element 34 may be coupled to a circuit board 38 within sensor housing 26. In some embodiments, sensing element 34 may be implemented as a conventional strain gauge sensor. The strain gauge sensor may be formed by thin film deposition on a flexible membrane. Circuit board 38 may include processing electronics to process signals generated by sensing element 34, and generate pressure information based on the signals. In addition, circuit board 38 may include telemetry circuitry for wireless telemetry with stimulator 14, external programmer 16, or both.

Sensor housing 26 may be made from a biocompatible material such as titanium, stainless steel or nitinol, or a polymeric material such as silicone or polyurethane. Another material for fabrication of sensor housing 26 is a two-part epoxy. An example of a suitable epoxy is a two-part medical implant epoxy manufactured by Epoxy Technology, Inc., mixed in a ratio of 10 grams of resin to one gram of activator. In general, sensor housing 26 contains no external openings, with the exception of the opening to receive flexible tube 28, thereby protecting sensing element 26 and circuit board 38 from the environment within bladder 24. The proximal, open end 34 of flexible tube 28 resides within sensor housing 26 while the distal, closed end 32 resides outside of the sensor housing. The opening in sensor housing 26 that receives open end 34 of flexible tube 28 may be sealed to prevent exposure of interior components.

Flexible tube 28 may be formed from a variety of flexible materials, including polyurethane or silicone. The flexibility of tube 28 permits it to conform to contours within bladder neck 23, and deform in response to pressure exerted urethra 20 by urinary sphincter 22 at bladder neck 23. In particular, urinary sphincter 22 exerts pressure inward against the outer wall of urethra 20. In turn, the inner wall of urethra 20 exerts pressure inward against the outer wall of flexible tube 28, causing the wall of the tube to deform and compress inward. In some embodiments, flexible tube 28 may be coated to avoid calcification.

Inward deformation of flexible tube 28 causes an elevation in the internal pressure of the tube. Sensing element 36 senses the elevation in pressure at open end 34 of flexible tube 28, and generates a pressure signal that represents the pressure level. Although end 34 is referred to as "open," it is sealed by sensing element 34. Consequently, deformation of flexible tube 28 causes volumetric changes in the tube, and hence pressure changes in the fluid 30 within the tube. Electronics on circuit board 38 generate pressure information based on the pressure signal. The pressure information can be used to evaluate the pressure level exerted by urinary sphincter 22.

The fluid 30 contained within flexible tube 28 may be a liquid or gas, or a combination of liquid and gas. For example, flexible tube 28 could be filled with saline, distilled water, oxygen, air, or any other biocompatible fluid. Preferably, the fluid 30 within flexible tube 28 is generally non-compressible. Fluid 30 tends to exhibit an elevation in pressure as the wall of tube 28 is deformed during constriction of urinary sphincter 22. Conversely, fluid 30 exhibits a reduction in pressure as urinary sphincter 22 relaxes. In each case, the pressure level is transduced by sensing element 36.

Flexible tube 28 may be provided with different dimensions selected for patients having different anatomical dimensions. In particular, implantable pressure sensor 12 may be constructed with a flexible tube 28 having different lengths of diameters. Different tube lengths may be necessary given the distance between the attachment site of sensor housing 26 and urinary sphincter 22, either to ensure that flexible tube 28 reaches the sphincter or does not extend too far down urethra 20. Multiple diameters may also be necessary to allow a dysfunctional sphincter 22 to close completely or to allow fluid-filled tube 28 to be placed into a narrow urethra 20. The dimensions may be fixed for a given pressure sensor 12, as a complete assembly. Alternatively, fluid tubes of different sizes may be attached to a pressure sensor housing 26 by a physician prior to implantation.

In general, for male patients, flexible tube 28 may have a length of less than approximately 9 cm and more preferably less than approximately 7 cm. For female patients, flexible tube 28 may have a length of less than approximately 7 cm and more preferably less than approximately 5 cm. In some embodiments, flexible tube 28 may have a length of approximately 0.5 cm to 3 cm. The length of tube 28 may vary according to the anatomy of the patient, and may vary between male, female and pediatric patients. In addition, tube 28 may have an outer diameter in a range of approximately 1 to 3 mm. The wall of tube 28 may be relatively thin to ensure sufficient deformation and conformability, yet thick enough to ensure structural integrity. As an example, the thickness of the wall of tube 28 may be in a range of approximately 0.1 mm to 0.3 mm.

Sensing element 36, in some embodiments, may be constructed as a membrane that carries a resistive strain gauge or piezoelectric element selected to be effective as a pressure transducer. Upon deformation of the membrane, in response to pressure levels within flexible tube 28, sensing element 36 produces an electrical signal. When sphincter 22 closes, the flexible tube 28 deforms and the pressure inside the tube increases. The higher pressure forces membrane in sensing element 36 to deform, thus producing an electrical signal change and enabling implanted pressure sensor 12 to measure sphincter closing pressure.

Attaching implantable pressure sensor 12 to the mucosal lining of bladder 24 may be accomplished in a variety of ways, but preferably is completed in a manner that will not excessively injure bladder 24 or otherwise cause excessive trauma during implantation. Preferably, attachment should cause limited inflammation and substantially no adverse physiological modification, such as tissue infection or a loss in structural integrity of bladder 24. However, it is desirable that implantable pressure sensor 12 also be attached securely to the attachment site in order to provide an extended period of measurement without prematurely loosening or detaching from the intended location.

As an example, sensor housing 26 may contain a vacuum cavity 39 that permits a vacuum to be drawn by a vacuum channel 40. The vacuum is created by a deployment device having a vacuum line in communication with vacuum channel 40. The vacuum draws a portion 42 of the mucosal lining 44 of bladder 24 into vacuum cavity 39. Once the portion 42 of mucosal lining 44 is captured within vacuum cavity 39, a fastening pin 46 is driven into the captured tissue to attach sensor housing 26 within bladder 24. Fastening pin 46 may be made from, for example, stainless steel, titanium, nitinol, or a high density polymer. The shaft of pin 46 may be smooth or rough, and the tip may be a sharp point to allow for easy penetration into tissue. Fastening pin 46 may be driven into housing 26 and the portion 42 of mucosal lining 44 under pressure, or upon actuation by a push rod, administered by a deployment device.

In some embodiments, fastening pin 46 may be manufactured from a degradable material that the breaks down over time, e.g. in the presence of urine, to release implantable pressure sensor 12 within a desired time period after attachment. In still another embodiment, implantable pressure sensor 12 may be attached without the use of a penetrating rod but with a spring-loaded clip to pinch trapped mucosal lining 44 within cavity 39. A variety of other attachment mechanisms, such as pins, clips, barbs, sutures, helical screws, surgical adhesives, and the like may be used to attach sensor housing 26 to mucosal lining 44 of bladder 24.

Figure 4:
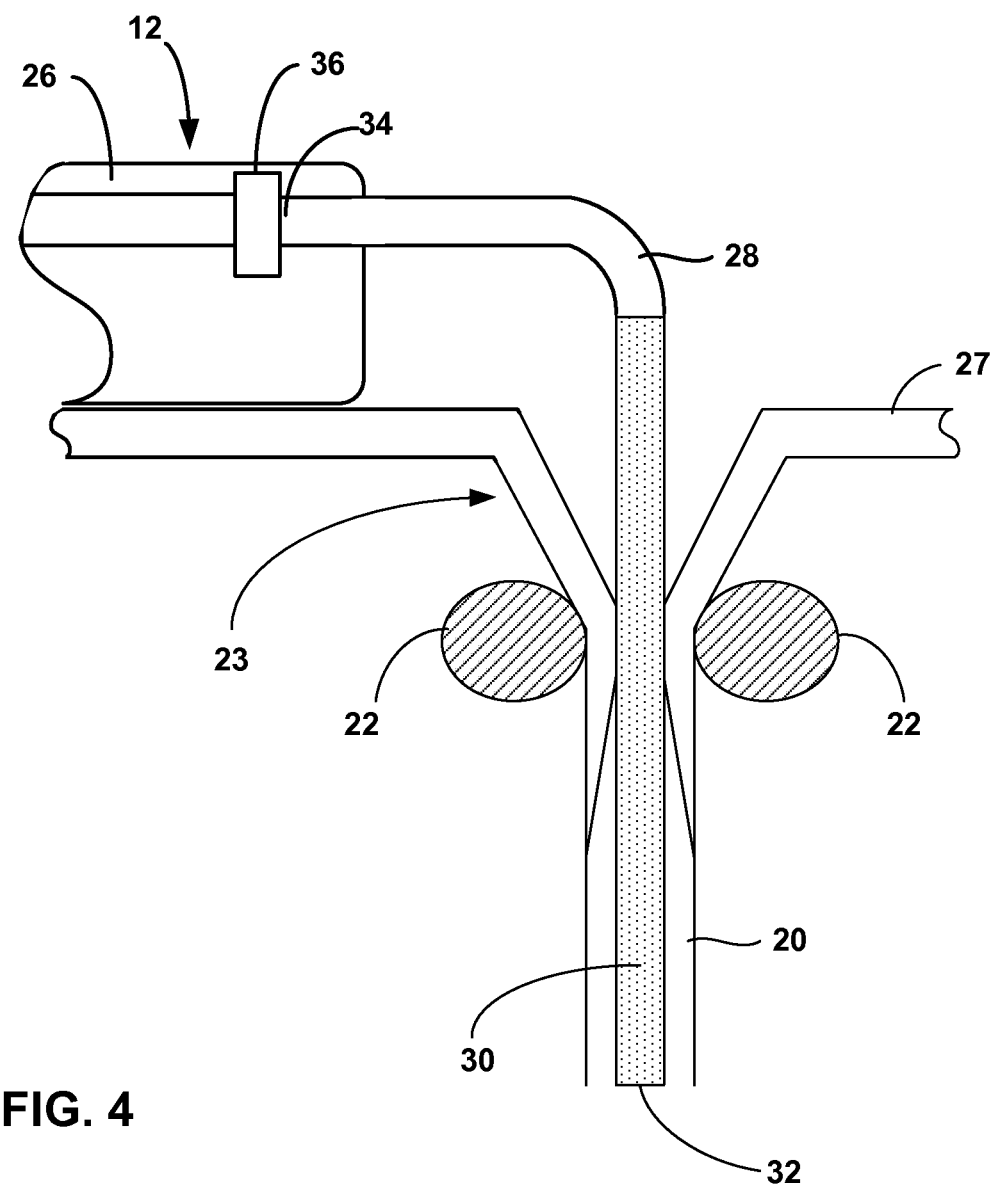
FIG. 4 is a schematic diagram illustrating placement of an implantable pressure sensor with a flexible tube extending through the internal urinary sphincter of a patient.

FIG. 4 is a schematic diagram illustrating placement of an implantable pressure sensor 12 with a flexible tube 28 extending through the urinary sphincter 22 of a patient 18. In the example of FIG. 4, flexible tube 28 leaves bladder 24 through bladder neck 23 and passes through internal urinary sphincter 22 as it enters urethra 20. In general, sphincter 22 is an annulus shaped muscle that surrounds the portion of urethra 20 below bladder neck 23 and constricts to make the urethral walls meet and thereby close urethra 20 to prevent involuntary urine leakage from bladder 24. Upon constriction of sphincter 22, the walls of urethra 20 close onto flexible tube 28 to increase the internal pressure of the tube, which provides a direct measurement of the closing pressure of sphincter 22. Because tube 28 has a circular cross-section and a small diameter, a closed sphincter 22 will still be able to substantially seal urethra 20 around tube 122.

When sphincter 22 is relaxed, in some embodiments, implantable pressure sensor 12 may be used to measure the pressure of fluid in urethra 20. The open sphincter 22 allows urine to be passed out of the urethra and patient 18. Flexible tube 28 is under the same pressure as the urethra and can allow implantable pressure sensor 12 to measure this urethral pressure. This may allow monitoring of urinary dysfunctions due to pressure during voiding events and may also be used by implantable stimulator 14 to detect the end of a voiding event by measuring decrease of urethral pressure as an indication of reduced urine flow.

As shown in FIG. 4, the placement of tube 28 does not significantly interfere with normal bladder function. Bladder function is unimpaired and fluid flow to urethra 20 can occur normally, as tube 28 allows enough room for urine to pass and exit bladder 24 via urethra 20. Due to varying sizes and shapes of patient anatomy, tube 28 may be manufactured in a variety of lengths and diameters.

Figure 5:
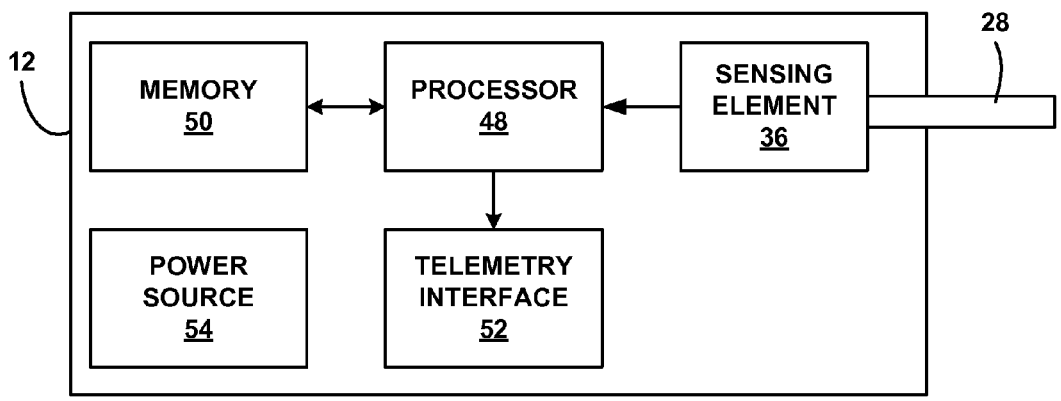
FIG. 5 is functional block diagram illustrating various components of an exemplary implantable pressure sensor.

FIG. 5 is functional block diagram illustrating various components of an exemplary implantable pressure sensor 12. In the example of FIG. 5, implantable pressure sensor 12 includes a sensing element 36, processor 48, memory 50, telemetry interface 52, and power source 54. Sensor 36 transforms mechanical deformation from tube 28 into electrical signals representative of closing pressure of urinary sphincter 22. The electrical signals may be amplified, filtered, and otherwise processed as appropriate by electronics within sensor 12, or circuitry associated with the sensor. In some embodiments, the signals may be converted to digital values and processed by processor 48 before being saved to memory 50 or sent to implantable stimulator 14 as pressure information via telemetry interface 52.

Memory 50 stores instructions for execution by processor 48 and pressure information generated by sensing element 36.

Pressure data may then be sent to implantable stimulator 14 or external programmer 16 for long-term storage and retrieval by a user. Memory 50 may include separate memories for storing instructions and pressure information. In addition, processor 48 and memory 50 may implement loop recorder functionality in which processor 48 overwrites the oldest contents within the memory with new data as storage limits are met, thereby conserving data storage resources within pressure sensor 12.

Processor 48 controls telemetry interface 52 to send pressure information to implantable stimulator 14 or programmer 16 on a continuous basis, at periodic intervals, or upon request from the implantable stimulator or programmer. Wireless telemetry may be accomplished by radio frequency (RF) communication or proximal inductive interaction of pressure sensor 12 with programmer 16.

Power source 54 delivers operating power to the components of implantable pressure sensor 12. Power source 54 may include a battery and a power generation circuit to produce the operating power. In some embodiments, the battery may be rechargeable to allow extended operation Recharging may be accomplished through proximal inductive interaction between an external charger and an inductive charging coil within sensor 12. In some embodiments, power requirements may be small enough to allow sensor 12 to utilize patient motion and implement a kinetic energy-scavenging device to trickle charge a rechargeable battery. In other embodiments, traditional batteries may be used for a limited period of time. As a further alternative, an external inductive power supply could transcutaneously power sensor 12 whenever pressure measurements are needed or desired.

Figure 6:
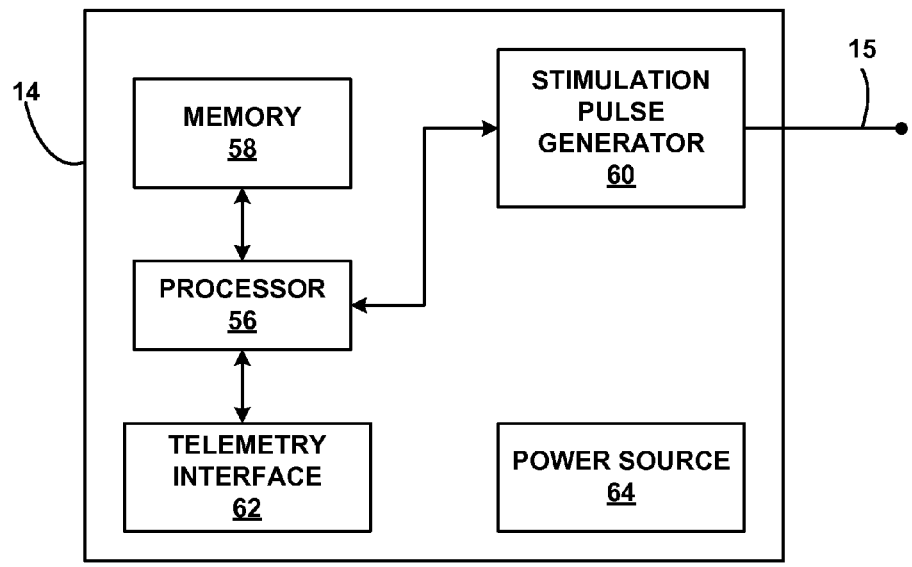
FIG. 6 is a functional block diagram illustrating various components of an implantable stimulator.

FIG. 6 is a functional block diagram illustrating various components of an implantable stimulator 14. In the example of FIG. 6, stimulator 14 includes a processor 56, memory 58, stimulation pulse generator 60, telemetry interface 62, and power source 64. Memory 58 stores instructions for execution by processor 56, stimulation therapy data, and pressure information received from pressure sensor 12 via telemetry interface. Pressure information is received from pressure sensor 12 and may be recorded for long-term storage and retrieval by a user, or adjustment of stimulation parameters, such as amplitude, pulse width or pulse rate. Memory 58 may include separate memories for storing instructions, stimulation parameter sets, and pressure information.

Processor 56 controls stimulation pulse generator 60 to deliver electrical stimulation therapy and telemetry interface 62 to send and receive information. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 100 microseconds and 1000 microseconds, and still more preferably between approximately 180 microseconds and 450 microseconds.

Based on pressure information received from sensor 12, processor 56 interprets the information and determines whether any therapy parameter adjustments should be made. For example, processor 56 may compare the pressure level to one or more thresholds, and then take action to adjust stimulation parameters based on the pressure level. Information may be received from sensor 12 on a continuous basis, at periodic intervals, or upon request from stimulator 14 or external programmer 16. Alternatively, or additionally, pressure sensor 12 may transmit pressure information when there is an abrupt change in the pressure level, e.g., at the onset of involuntary leakage.

Processor 56 modifies parameter values stored in memory 58 in response to pressure information from sensor 12, either independently or in response to programming changes from external programmer 16. Stimulation pulse generator 60 provides electrical stimulation according to the stored parameter values via a lead 15 implanted proximate to a nerve, such as a sacral nerve. Processor 56 determines any parameter adjustments based on the pressure information obtained form sensor 12, and loads the adjustments into memory 58 for use in delivery of stimulation.

As an example, if the pressure information indicates an inadequate sphincter closing pressure, processor 56 may increase the amplitude, pulse width or pulse rate of the electrical stimulation applied by stimulation pulse generator 60 to increase stimulation intensity, and thereby increase sphincter closing pressure. If sphincter closing pressure is adequate, processor 56 may implement a cycle of downward adjustments in stimulation intensity until sphincter closing pressure becomes inadequate, and then incrementally increase the stimulation upward until closing pressure is again adequate. In this way, processor 56 converges toward an optimum level of stimulation. Although processor 56 is described in this example as adjusting stimulation parameters, it is noted that the adjustments alternatively may be generated by external programmer 16 and transmitted to stimulator 14 as parameter or program changes.

The adequacy of closing pressure is determined by reference to the pressure information obtained from sensor 12. Sphincter pressure may change due to a variety of factors, such as an activity type, activity level or posture of the patient 18. Hence, for a given set of stimulation parameters, the efficacy of stimulation may vary in terms of sphincter pressure, due to changes in the physiological condition of the patient. For this reason, the continuous or periodic availability of pressure information from implantable sensor 12 is highly desirable.

With this pressure information, stimulator 14 is able to respond to changes in sphincter pressure with dynamic adjustments in the stimulation parameters delivered to the patient 18. In particular, processor 56 is able to adjust parameters in order to cause constriction of sphincter 22 and thereby avoid involuntary leakage. In some cases, the adjustment may be nearly instantaneous, yet prevent leakage. As an example, if patient 18 laughs, coughs, or bends over, the resulting force on bladder 24 could overcome the closing pressure of urinary sphincter 22. If pressure sensor 12 indicates an abrupt change in sphincter pressure, however, stimulator 14 can quickly respond by more vigorously stimulating the sacral nerves to increase sphincter closing pressure.

In general, if sphincter 22 is not constricting enough to effectively close urethra 20, processor 56 may dynamically increase the level of therapy to be delivered. Conversely, if sphincter 22 is consistently achieving effective constriction, processor 56 may incrementally reduce stimulation, e.g., to conserve power resources.

As in the case of sensor 12, wireless telemetry in stimulator 14 may be accomplished by radio frequency (RF) communication or proximal inductive interaction of pressure stimulator 14 with implantable pressure sensor 12 or external programmer 16. Accordingly, telemetry interface 62 may be similar to telemetry interface 52. Also, power source 64 of stimulator 14 may be constructed somewhat similarly to power source 54. For example, power source 64 may be a rechargeable or non-rechargeable battery, or alternatively take the form of a transcutaneous inductive power interface.

Figure 7:
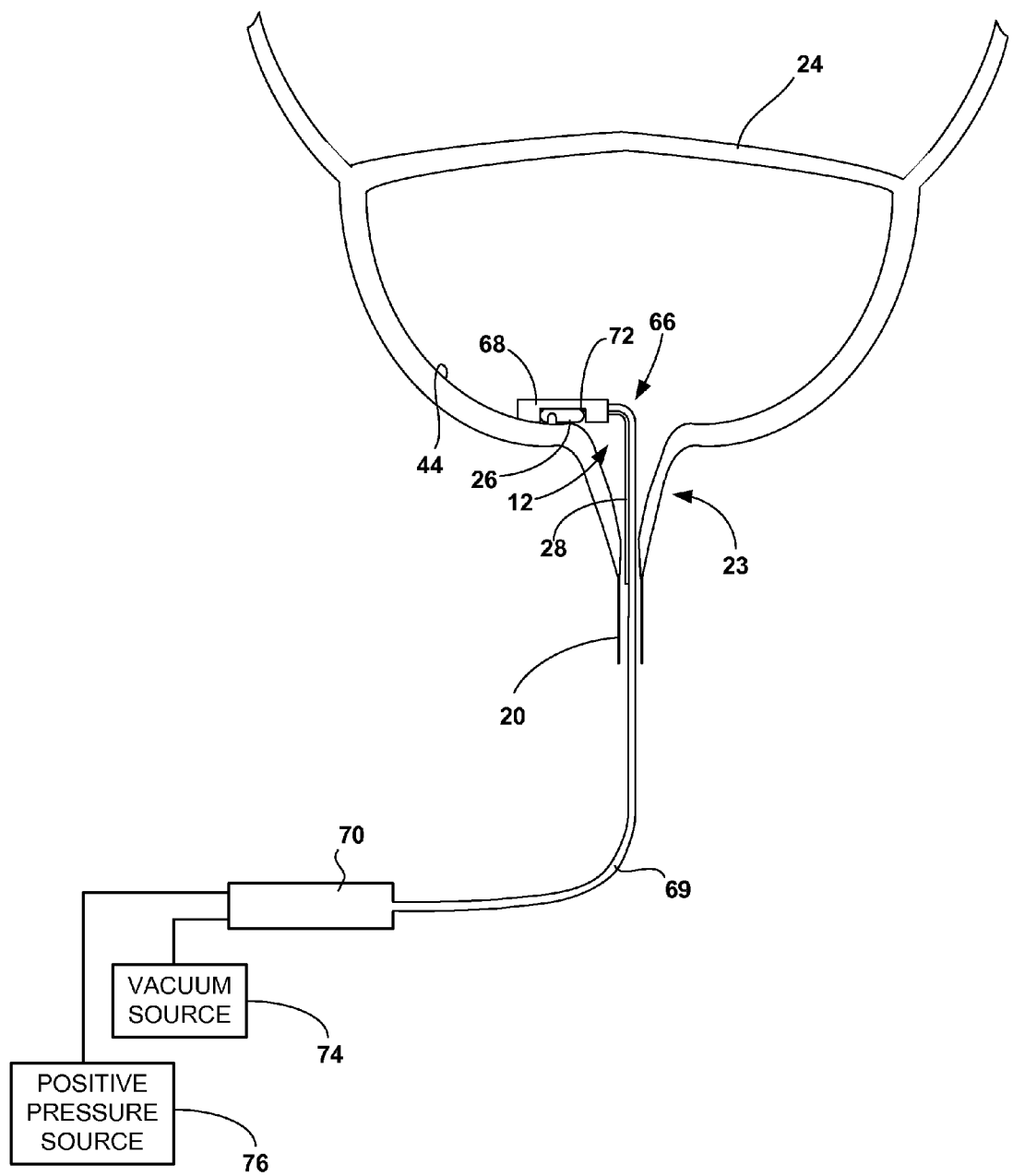
FIG. 7 is a schematic diagram illustrating cystoscopic deployment of an implantable pressure sensor via the urethra.

FIG. 7 is a schematic diagram illustrating cystoscopic deployment of an implantable pressure sensor 12 via the urethra 20 using a deployment device 66. Pressure sensor 12 may be surgically implanted. However, cystoscopic implantation via urethra is generally more desirable in terms of patient trauma, recovery time, and infection risk. Pressure sensors 12 may be implanted in a variety of ways, using a variety of different deployment and attachment structures. Accordingly, the embodiment depicted in FIG. 7 is exemplary and not limiting of the invention as broadly embodied herein.

In the example of FIG. 7, deployment device 66 includes a distal head 68, a delivery sheath 69 and a control handle 70. Deployment device 66 may be manufactured from disposable materials for single use applications or more durable materials for multiple applications capable of withstanding sterilization between patients. As shown in FIG. 7, distal head 68 includes a cavity that retains sensor housing 26 of implantable pressure sensor 12 for delivery to a desired attachment site within bladder 24.

Sensor housing 26 may be held within cavity 72 by a friction fit, vacuum pressure, or a mechanical attachment. In each case, once distal head 68 reaches the attachment site, sensor housing 26 may be detached. Sheath 69 is attached to distal head 68 and is steerable to navigate urethra 20 and guide the distal head into position. In some embodiments, sheath 69 and distal head 68 may include cystoscopic viewing components to permit visualization of the attachment site. In other cases, external visualization techniques such as ultrasound may be used. Sheath 68 may include one or more steering mechanisms, such as wires, shape memory components, or the like, to permit the distal region adjacent distal head 68 to turn abruptly for access to the mucosal lining of bladder 24.

A control handle 70 is attached to sheath 69 to aid the physician in manually maneuvering deployment device 66 throughout urethra 20 and bladder 24. Control handle 70 may have a one or more controls that enable the physician to contort sheath 69 and allow for deployment device 66 to attach pressure sensor housing 26 to the mucosal lining of bladder 24 and then release the sensor housing to complete implantation. In other embodiments, pressure sensor housing 26 may be attached sub-mucosally to the muscle wall of bladder 24 for more secure attachment. A vacuum source 74 supplies negative pressure to a vacuum line within sheath 69 to draw tissue into the vacuum cavity defined by sensor housing 66. A positive pressure source 76 supplies positive pressure to a drive a fastening pin into the tissue captured in the vacuum cavity.

Deployment device 66 enters patient urethra 20 to deliver pressure sensor 12 and implant it within bladder 24. First, the physician must guide distal head 68 through the opening of urethra 20 in patient 18. Second, distal head 68 continues to glide up urethra 20 and past the relaxed internal sphincter 22. Distal head 300 is then pushed through bladder neck 23 and into bladder 24, for access to an appropriate site to attach pressure sensor 12. Using actuators built into control handle 70, sheath 69 is bent to angle distal head 68 into position. Again, sheath 69 may be steered using control wires, shape memory alloys or the like.

As pressure sensor 12 is guided into place against the mucosal wall 44 of bladder 24, a physician actuates control handle 70 to attach sensor 12 to mucosal wall 44 and then release the attached sensor. Upon attachment, pressure sensor 12 is implanted within bladder 24 of patient 18 and deployment device 66 is free to exit the bladder. Exemplary methods for attachment and release of sensor 12, including the use of both vacuum pressure and positive pressure, will be described in greater detail below. Although FIG. 7 depicts cystoscopic deployment of pressure sensor 12, surgical or laparoscopic implantation techniques alternatively may be used.

Figure 8:
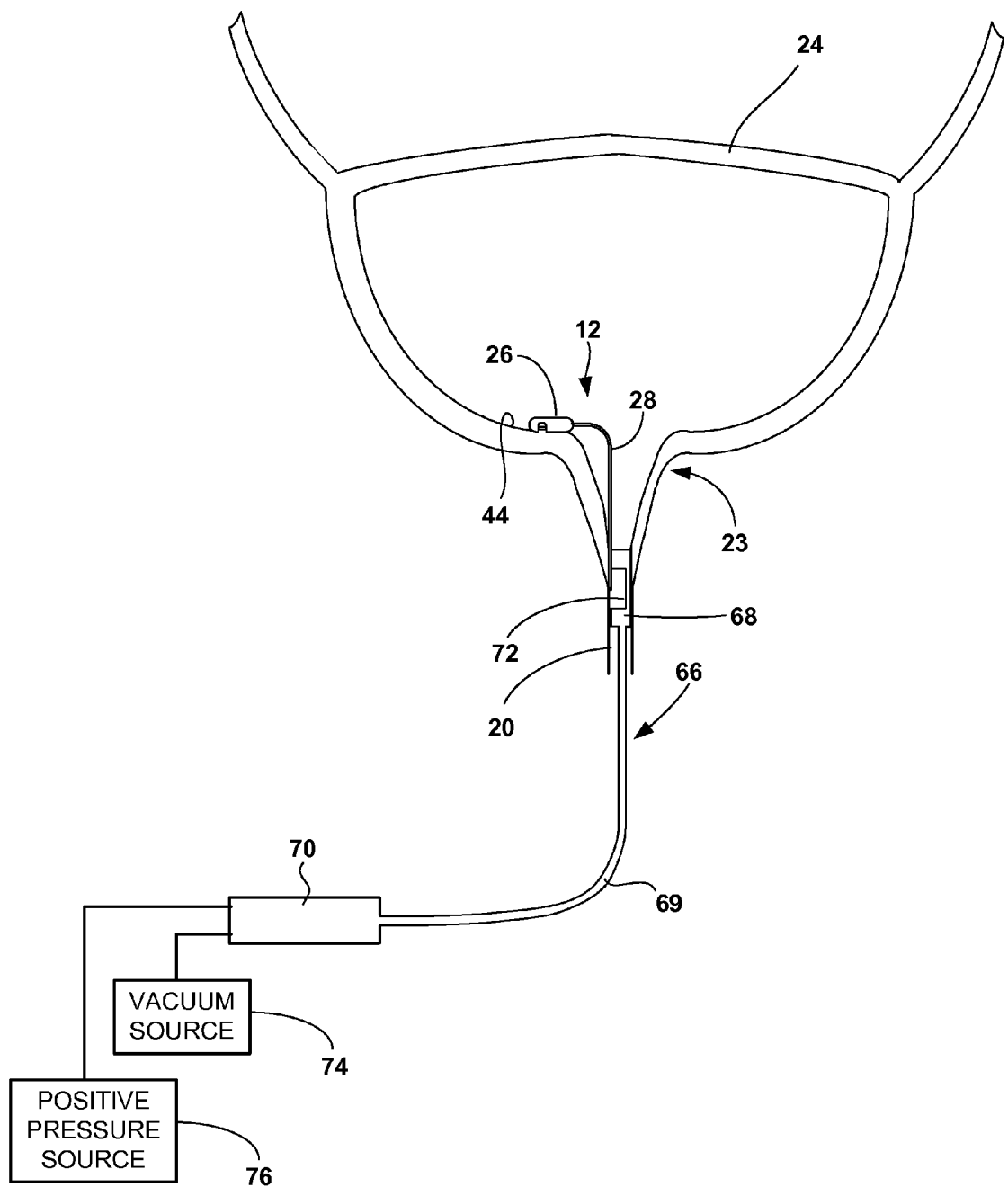
FIG. 8 is a schematic diagram illustrating retraction of a deployment device upon fixation of a pressure sensor within a patient's urinary tract.

FIG. 8 is a schematic diagram illustrating retraction of deployment device 66 upon fixation of pressure sensor 12 within the urinary tract of patient 18. Once the sensor 12 is released, flexible tube 28 remains attached to sensor housing 26. During removal of deployment device 66, tube 28 maintains its position within bladder neck 23 adjacent sphincter 22. As deployment device 66 is removed, tube 28 passes through a guide channel formed in the deployment device. The guide channel ensures that flexible tube 28 remains pinned between distal head 68 and the wall of bladder 24.

As distal head 68 slides through sphincter 22 and urethra 20, however, flexible tube 28 releases from deployment device 66 and is left in place within the urethra in the region proximate urinary sphincter 22. Deployment device 66 may then be completely withdrawn past the external urinary sphincter and out of the remainder of urethra 20. In the example of FIG. 8, flexible tube 28 is suspended by device housing 26, which is attached to mucosal wall 44, and is held in place by pressure exerted against the urethral wall by urinary sphincter 22. In other embodiments, tube 28 may be kept in place using other techniques such as actively fixing tube 28 to the side of urethra 20, e.g., with sutures or other anchor mechanisms.

In one embodiment, sheath 69 and distal head 68 may be disposable. Disposable devices that come into contact with patient 18 tissues and fluids greatly decrease the possibility of infection in implantable devices. Control handle 70 does not come into contact with body fluids of patient 18 and may be used for multiple patients. In another embodiment, the entire deployment device 66 may be manufactured out of robust materials intended for multiple uses. The device would then need to be sterilizable between uses. In still a further embodiment, the features of distal head 68 may be incorporated into pressure sensor 12. In this configuration, pressure sensor 12 may be larger in size but would include the necessary elements for attachment within the device. After attachment, the entire sensor would detach from sheath 69, making removal of deployment device 66 easier on patient 18.

After the useful life of implantable pressure sensor 12 is complete or it is no longer needed within patient 18, it can be removed from patient 18 in some manner. As an example, deployment device 66 may be reinserted into patient 18, navigated into bladder 24, and reattached to pressure sensor 12. Deployment device 66 may then be withdrawn from the bladder 24 and urethra 20, explanting sensor 12, including housing 26 and flexible tube 28, from patient 18. In another embodiment, as mentioned with respect to FIG. 3, the attachment method of pressure sensor 12 to bladder 24 may involve degradable materials, such as a biodegradable fixation pin. After a certain period of time exposed to urine in the bladder 24, the fixation material may structurally degrade and allow pressure sensor 12 to be released from the mucosal wall 44 of bladder 24. In some embodiments, sensor 12 may be sized sufficiently small to follow urine out of the bladder, urethra, and body during a voiding event. In other embodiments, sensor housing 26 or tube 28 may carry a suture-like loop that can be hooked by a catheter with a hooking element to withdraw the entire assembly from patient 18 via urethra 20. In still further embodiments, such a loop may be long enough to extend out of the urethra, so that the loop can be grabbed with an external device or the human hand to pull the sensor 12 out of the patient.

Figure 9:
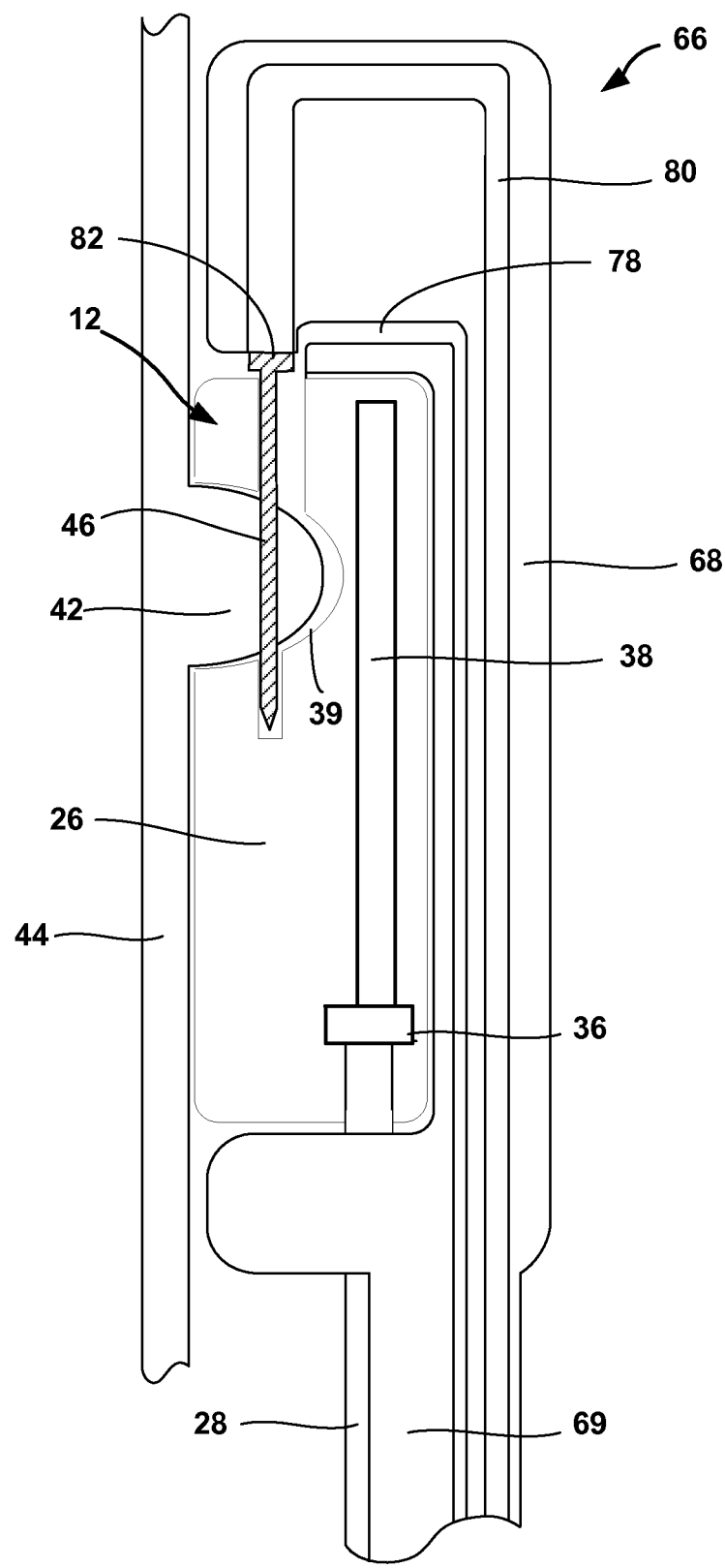
FIG. 9 is a cross-sectional side view of a deployment device during deployment and fixation of a pressure sensor.

FIG. 9 is a cross-sectional side view of distal head 68 of deployment device 66 during deployment and fixation of pressure sensor 12. In the example of FIG. 9, distal head 68 receives a vacuum line 78 and a positive pressure line 80. Vacuum line 78 is coupled to vacuum source 74 via a tube or lumen extending along the length of sheath 69. Similarly, positive pressure line 80 is coupled to positive pressure source 76 via a tube or lumen extending along the length of sheath 69. Vacuum line 78 is in fluid communication with vacuum cavity 39, and permits the physician to draw a vacuum and thereby capture a portion 42 of mucosal lining 44 within the vacuum cavity. Positive pressure line 80 permits the physician to apply a pulse of high pressure fluid, such as a liquid or a gas, to drive fixation pin 46 into sensor housing 26 and through the portion 42 of mucosal lining 44. Pin 46 thereby fixes sensor housing 26 to mucosal lining 44. In some embodiments, a membrane mounted over an opening of positive pressure line 80 may be punctured by pin 46.

Flexible tube 28 resides within a channel of sheath 69 prior to detachment or sensor 12 from distal head 68. Once fixation pin 46 attaches sensor 12 to bladder 24, vacuum line 78 is no longer needed. However, in some embodiments, vacuum line 78 may be used to detach pressure sensor 12 from distal head 68 of deployment device 66. By terminating vacuum pressure, or briefly applying positive pressure through vacuum line 78, for example, head 68 may separate from sensor 12 due to the force of the air pressure. In this manner, vacuum line 78 may aid in detachment of sensor 12 prior to withdrawal of deployment device 66.

As described previously in FIG. 3, fixation pin 46 punctures mucosal lining 44 for fixation of sensor 12. While the force of this fixation may vary with patient 18, deployment device 66 provides adequate force for delivery of pin 46. In an exemplary embodiment, positive pressure line 80 is completely sealed and filled with a biocompatible fluid (such as water, saline solution or air). Sealing the end of positive pressure line 80 is a head 82 on fixation pin 46. Head 82 is generally able to move within positive pressure line 80 much like a piston. Force to push fixation pin 46 through the portion 42 of mucosal lining 44 captured in vacuum cavity 39 is created by application of a pulse of increased fluid pressure within positive pressure line 80. For example, the physician may control positive pressure source 76 via control handle 70. This simple delivery method may provide high levels of force, allow multiple curves and bends in sheath 69, and enable a positive pressure line 80 of many shapes and sizes.

In an alternative embodiment, a flexible, but generally incompressible, wire may be placed within positive pressure line 80 and used as a push rod to force fixation pin 46 through the captured portion 42 of mucosal lining 44. This wire presents compressive force from control handle 70 directly to the head 82 of fixation nail 46. This method may eliminate any safety risk of pressurized fluids entering patient 18 or, in some embodiments, permit refraction of pin 46 after an unsuccessful fixation attempt. The flexible wire may be attached to pin 46 and pulled back to remove the pin from capture mucosal tissue 42. The flexible wire may be sheared from fixation nail 46 for detachment purposes as distal head 68 releases sensor 12. This detachment may be facilitated by a shearing element or low shear stress of the wire.

In FIG. 9, deployment device 66 illustrates flexible tube 28 on the same end of housing 26 as sheath 69, while the fixation structures are located in the opposite, or distal end of distal head 68. In some embodiments, it may be necessary for pressure sensor 12 to be deployed with tube 28 located at the distal end of head 68 and the fixation structures located near sheath 69. In still other embodiments, the fixation structures and tube 28 may be located on the same end of pressure sensor 12.

In some embodiments, deployment device 66 may include a small endoscopic camera in the distal head 68. The camera may enable the physician to better guide deployment device 66 through urethra 20, past sphincter 22, and to a desired attachment location of bladder 24 in less time with more accuracy. Images may be displayed using video fed to a display monitor.

Figure 10:
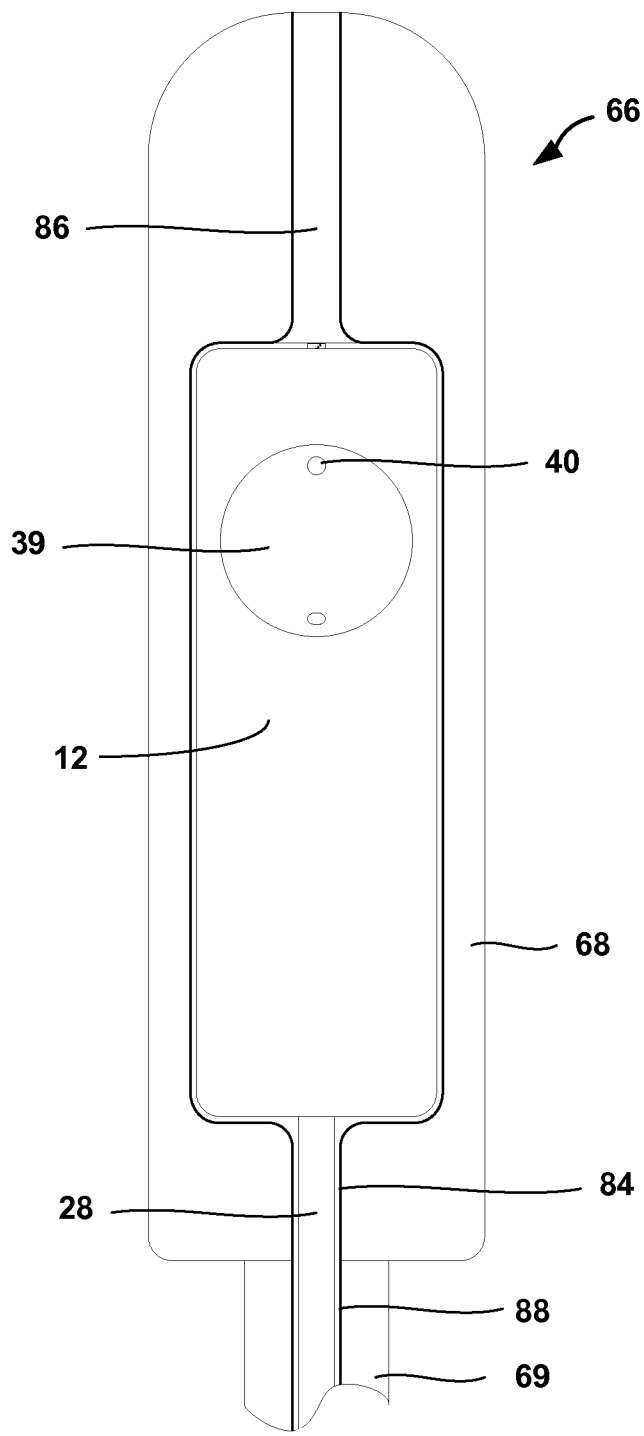
FIG. 10 is a cross-sectional bottom view of the deployment device of FIG. 10 before attachment of the pressure sensor.

FIG. 10 is a cross-sectional bottom view of the deployment device 66 of FIG. 10 before attachment of pressure sensor 12. As shown in FIG. 10, distal head 68 includes proximal tube channel 84 to accommodate flexible tube 28 during placement of sensor 12 and distal tube channel 86 to accommodate the flexible tube during retraction of deployment device 66. In addition, sheath 69 includes a sheath channel 88 to accommodate flexible tube 28. Channels 84, 86, 88 serve to retain tube 28 during delivery of sensor 12 to an attachment site.

Distal head 68 is rounded on both sides at the distal end to permit easier entry of deployment device into areas of patient 18. Head 68 may also be lubricated before delivery to facilitate ease of navigation. On the proximal end of head 68, proximal tube channel 84 runs through the head for unimpeded removal of tube 28 during detachment of pressure sensor 12. This channel may be U-shaped, e.g., closed on 3 sides. In some embodiments, proximal tube channel 84 may be an enclosed hole in which tube 28 resides and glides through upon deployment device 30 removal.

Sheath channel 88 is formed within sheath 69 to allow tube 28 to stay in place during delivery of pressure sensor 12. In this embodiment, tube 28 is only partially retained within channel 88. In some embodiments, sheath channel 88 may be deeper to allow tube 28 to lie completely within sheath 69, whereas others may include a completely enclosed channel that tube 28 must glide out of after attachment.

Distal channel 86 in distal end of head housing 68 is not used by tube 28 before attachment. The purpose of this open channel is to allow tube 28 to glide through it while head 68 is removed from bladder 24. As head 68 slides back past pressure sensor 12, tube 28 will slide through channel 86 and head housing 68 will keep tube 28 between the wall of bladder 24 and head 68 until head 68 has been removed beyond sphincter 22. Tube 28 may then be ensured correct placement through sphincter 22.

Some embodiments of tube 28 include multiple length and diameter combinations which would lead to modifications in channels 84, 86 and 88. The channels herein may be of different diameters or lengths to properly house tube 28. One embodiment may include flexible housing channels to accommodate a wide variety of tube 28 dimensions. Further embodiments of deployment device 30 may contain modified channel locations in head housing 68. These locations may be needed to place tube 28 in different locations, particularly at different sphincter sites as in some embodiments.

Figure 11:
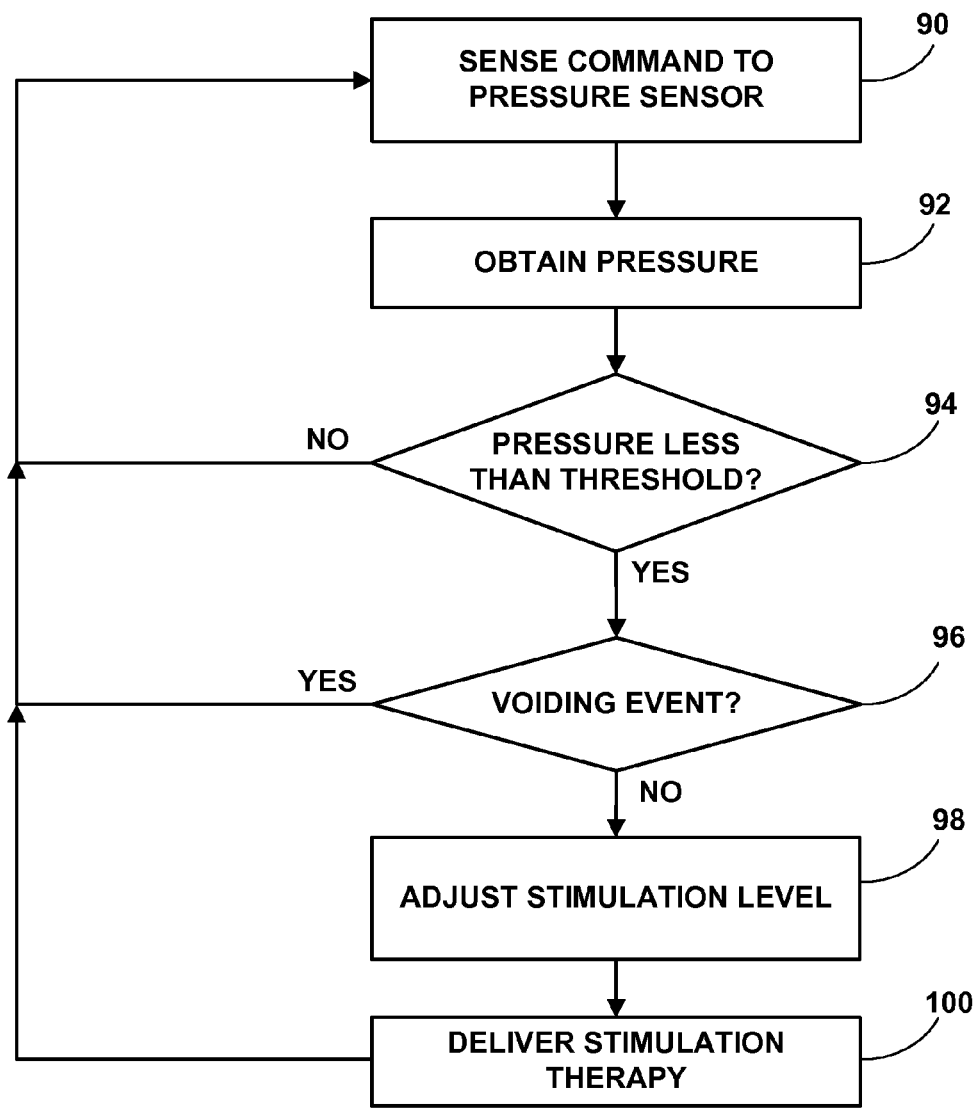
FIG. 11 is a flow chart illustrating a technique for delivery of stimulation therapy based on closed loop feedback from an implantable pressure sensor.

FIG. 11 is a flow chart illustrating a technique for delivery of stimulation therapy based on closed loop feedback from an implantable pressure sensor. In the example of FIG. 11, implantable stimulator 14 requires information from implantable pressure sensor 12 and external programmer 16. The flow of events begins with implantable stimulator 14 communicating with implantable pressure sensor 12 and sending a command to sense the pressure of sphincter 22 (90). In other embodiments, pressure sensor 12 may voluntarily sense pressure on a periodic basis.

The pressure sensor 12 subsequently acquires a pressure measurement and delivers the data to implantable stimulator 14 (92), e.g., by wireless telemetry. Alternatively, the sense data may be transmitted from sensor 12 to external programmer 16. Upon receiving the pressure data, implantable stimulator 14 calibrates the data and compares it to a determined minimum pressure threshold (94). If the measured pressure is higher than the threshold, the loop begins again. If the pressure is lower than the threshold, the flow continues to the next step of stimulation.

Stimulator 14 and programmer 16 may receive sense data from sensor 12 in some embodiments. For example, stimulator 14 may react to instantaneous changes in pressure level, while programmer 16 may react to changes in pressure level over a period of time, e.g., trend data. Alternatively, either stimulator 14 or programmer 16 may be configured to react to instantaneous and trending pressure level changes.

In some embodiments, implantable stimulator 14 may communicate with external programmer 16 to check if patient 18 has desired to void the contents of bladder 24 (96). If patient 18 has signaled a voiding event, stimulation is skipped and the process begins again. In the case of no voiding event desired, sphincter 22 is not providing adequate closing pressure and needs to be stimulated. Implantable stimulator 14 next performs the necessary tasks to adjust the level of stimulation from stimulation pulse generator 60 (98), and thereby increase sphincter closing pressure. Stimulator 14 concludes the loop by delivering electric stimulation therapy to the nerve that innervates sphincter 22 (100). After stimulation therapy has commenced, the loop begins again to continue appropriate therapy to patient 18.

In some embodiments, pressure sensor 12 may be used exclusively for monitoring pressure without providing feedback for stimulation therapy. In this case, the process represented in FIG. 11 would be much simpler and only include collecting data and sending it to an external programmer (90 and 92). Pressure may be measured continuously, intermittently or at the request of external programmer 16. These embodiments may be used for disease diagnosis or condition monitoring and may provide a patient to avoid frequent clinic visits and uncomfortable procedures. In some embodiments, the pressure measurements may form part of an automated voiding diary that records voluntary voiding events, involuntary voiding events, and urinary sphincter and urethral pressure levels prior to, contemporaneous with, of after such an event.

Although the invention may be especially applicable to sensing urinary sphincter pressure, the invention alternatively may be applied more generally to other sphincters within the patient, such as the lower esophageal sphincter (LES) or pyloric sphincter. In addition, in those instances, the invention may be adapted to support electrical stimulation of other body organs, such as the stomach or intestines, e.g., for treatment of obesity or gastric mobility disorders. Not only may stimulation of certain nerves allow for the proper closure of a sphincter, but nerve stimulation may be able to modify stomach contractions or intestinal contractions based upon pressure measurements at those sites. Pressure feedback from the implantable pressure sensor may provide the most effective therapy for some patients, e.g., in the form of biofeedback that aids the patient in self-regulating bladder control. Also, the invention need not be limited to neurostimulation, and may be applied to stimulate other tissue, including muscle tissue.

Various embodiments of the described invention may include processors that are realized by microprocessors, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or non-voltatile memory, including random access memory (RAM), read only memory (ROM), electronically programmable memory (EPROM or EEPROM), or flash memory. Each storage option may be chosen depending on the embodiment of the invention. While the implantable stimulator and implantable pressure sensor ordinarily will contain permanent memory, a patient or clinician programmer may contain a more portable removable memory type to enable easy data transfer for offline data analysis.

Many embodiments of the invention have been described. Various modifications may be made without departing from the scope of the claims. For example, although the invention has been generally described in conjunction with implantable neurostimulation devices, a flexible tube sensor may also be used with other implantable medical devices, such as electrical muscle stimulation devices, functional electrical stimulation (FES) devices, and implantable drug delivery devices, each of which may be configured to treat incontinence or other conditions or disorders. These and other embodiments are within the scope of the following claims.

The invention claimed is:

1. An implantable pressure sensor comprising:
a housing;
a flexible tube containing fluid extending from the housing to a distal end; and
a sensing element mounted within the housing that senses a pressure level exerted by a sphincter on the flexible tube at a region of the tube spaced from the distal end when the tube is placed proximate to the sphincter; and
a processor adapted to receive the pressure level exerted by the sphincter sensed by the sensing element and transmit the pressure level exerted by the sphincter to an implantable stimulator configured to modulate the pressure level exerted by the sphincter based on a threshold pressure.

2. The sensor of claim 1, further comprising a fixation mechanism to position the flexible tube proximate the sphincter within a patient.

3. The sensor of claim 2, wherein the fixation mechanism is positioned to attach the housing to an inner wall of a bladder of the patient.

4. The sensor of claim 1, wherein the flexible tube includes a closed end and an open end, and the sensing element is disposed at the open end.

5. The sensor of claim 4, wherein the sensing element includes a flexible membrane that generates an electrical signal based on deformation of the membrane by pressure within the flexible tube.

6. The sensor of claim 5, wherein the flexible membrane includes a strain gauge sensor.

7. The sensor of claim 1, wherein the flexible tube has a length of less than approximately 7 cm and an outer diameter of approximately 1 to 3 mm.

8. The sensor of claim 1, wherein the implantable pressure sensor includes a housing, the tube extending from the housing, and the fixation mechanism is positioned to attach the housing to an inner wall of a bladder of the patient.

9. The sensor of claim 1, further comprising a telemetry circuit configured to be controlled by the processor to transmit the pressure level exerted by the sphincter to the implantable stimulator.

10. The sensor of claim 1, wherein the flexible tube comprises a plurality of flexible tubes containing fluid and extending from the housing to distal ends thereof, wherein the flexible tubes are configured to be disposed at different positions within a urinary tract.

11. The sensor of claim 1, wherein the sensing element senses a pressure level exerted by a urinary sphincter within the patient, and the implantable stimulator provides electrical stimulation to control urinary incontinence.

12. A method comprising:
sensing, with an implantable pressure sensor comprising a housing, a flexible tube containing fluid extending from the housing to a distal end, and a sensing element mounted within the housing, a pressure level exerted by a sphincter on the flexible tube at a region of the tube spaced from the distal end when the tube is placed proximate to the sphincter; and
transmitting the pressure level exerted by the sphincter to an implantable stimulator configured to modulate the pressure level exerted by the sphincter based on a threshold pressure.

13. The method of claim 12, wherein the flexible tube includes a closed end and an open end, and the sensing element is disposed at the open end.

14. The method of claim 12, wherein the sensing element includes a flexible membrane that generates an electrical signal based on deformation of the membrane by pressure within the flexible tube.

15. The method of claim 14, wherein the flexible membrane includes a strain gauge sensor.

16. The method of claim 12, wherein the flexible tube has a length of less than approximately 7 cm and an outer diameter of approximately 1 to 3 mm.

17. The method of claim 12, further comprising fixing the housing to an inner wall of a bladder of a patient.

18. The method of claim 12, wherein transmitting the pressure level exerted by the sphincter comprises transmitting the pressure level exerted by the sphincter from the sensor to the implantable stimulator via wireless telemetry.

19. The method of claim 12, further comprising transmitting the pressure level exerted by the sphincter to an external programmer, wherein the external programmer adjusts one or more parameters of electrical stimulation delivered by the implantable stimulator based on the transmitted pressure level exerted by the sphincter.

20. The method of claim 12, wherein sensing the pressure level exerted by the sphincter comprises sensing a pressure level exerted by a urinary sphincter within a patient, and wherein the implantable stimulator is configured to deliver electrical stimulation to control urinary incontinence.

21. The method of claim 12, further comprising modulating the pressure level exerted by the sphincter with the implantable stimulator based on the threshold pressure.

* * * * *